United States Patent [19]
Lane

[11] Patent Number: 5,940,891
[45] Date of Patent: Aug. 24, 1999

[54] GOGGLE MOUNTING SYSTEM WITH REMOVABLE EYELET

[75] Inventor: Abbott Atwood Lane, Dayton, Ohio

[73] Assignee: Firequip Helmets, Inc., Dayton, Ohio

[21] Appl. No.: 08/933,262

[22] Filed: Sep. 18, 1997

[51] Int. Cl.$^6$ ........................................... A61F 9/02
[52] U.S. Cl. ........................ 2/426; 2/5; 2/10; 351/155
[58] Field of Search ........................... 2/5, 6.3, 6.7, 422, 2/424, 15, 10, 452, 426; 24/196, 615, 625; 351/15.5

[56] References Cited

U.S. PATENT DOCUMENTS

| | | | |
|---|---|---|---|
| 2,267,558 | 12/1941 | Fernberg | 24/625 |
| 3,258,534 | 6/1966 | Goldsworthy | 179/1 |
| 3,273,163 | 9/1966 | Andrews | 2/3 |
| 3,373,444 | 3/1968 | Militello | 2/10 |
| 3,703,750 | 11/1972 | Irwin, Jr. | 24/265 R |
| 4,193,133 | 3/1980 | Laibach et al. | 2/10 |
| 4,276,657 | 7/1981 | Montesi | 2/422 |
| 4,521,831 | 6/1985 | Thayer | 362/32 |
| 4,686,712 | 8/1987 | Spiva | 2/10 |
| 4,764,989 | 8/1988 | Bourgeois | 2/452 |
| 4,788,724 | 12/1988 | Lazzeroni et al. | 2/422 |
| 4,796,308 | 1/1989 | Bourgeois | 2/243 R |
| 4,907,582 | 3/1990 | Meyerrose | 128/201.11 |
| 5,012,528 | 5/1991 | Pernicka et al. | 2/10 |
| 5,052,054 | 10/1991 | Birum | 2/10 |
| 5,226,181 | 7/1993 | Polednak et al. | 2/422 |
| 5,291,880 | 3/1994 | Almovist et al. | 2/5 |
| 5,341,516 | 8/1994 | Keim | 2/452 |
| 5,347,655 | 9/1994 | Garrett | 2/10 |
| 5,355,562 | 10/1994 | Matoba et al. | 24/615 |
| 5,365,615 | 11/1994 | Piszkin | 2/422 |

OTHER PUBLICATIONS 2 enclosed photographs showing a system of "D" rings for retaining the strap of a pair of goggles.

*Primary Examiner*—Diane L. Oleska
*Assistant Examiner*—Katherine Moran
*Attorney, Agent, or Firm*—Thompson Hine & Flory LLP

[57] ABSTRACT

A goggle mounting system for retaining a pair of goggles to the lower edge of a helmet or the like. The goggle retention system comprises a plurality of clips, each clip having a base mounted to a helmet, and a removable eyelet shaped to receive and retain the goggles. Each base has an oblong slot extending therethrough and is shaped to receive and retain an associated eyelet. Each base further includes a pair of transverse locking notches and a helical camming surface extending between the slot and the notches. Each eyelet includes a generally circular ring to retain the goggle strap, and a pair of spaced, parallel legs extending from the ring. Each eyelet further includes a pair of opposed, spaced feet at the ends of the legs. The feet are shaped to pass through the slot when the feet are oriented lengthwise of the slot. An eyelet is attached to an associated base by passing the feet of the eyelet through the slot of the base and rotating the eyelet so that the narrowing width of the slot urges the legs closer together causing the legs to exert a reactive force against the inside walls of the slot, thereby securing the eyelet to the base, and securing the strap in the eyelet. The system of the present invention allows the goggles to be easily attached or released by simple hand manipulation.

27 Claims, 3 Drawing Sheets

GOGGLE MOUNTING SYSTEM WITH REMOVABLE EYELET

BACKGROUND

The present invention relates to a headgear and more particularly, a goggle mounting system for retaining a pair of goggles to a firefighter helmet or the like.

Firefighters are often required to operate in an environment that poses a safety hazard to their eyes and faces. Extreme temperatures, loose debris, smoke, water and toxic chemicals may all be encountered during various operations. For this reason, goggles, in conjunction with a helmet, are often utilized to protect the firefighter from such an inhospitable environment. Because of the importance of goggles to the firefighter, it is important to have the goggles readily available for use. It is known in the art to provide for a plurality of goggle-receiving rings about the perimeter of the helmet to receive the goggle strap. Typically, rings are secured to the helmet by screws or bolts. In this manner, the goggles may be stored on the crown of the helmet when not in use, and the strap is retained within the rings. When a firefighter wishes to use goggles attached in that manner, the goggles may be pulled away from the crown, passed over the brim of the helmet, and placed over the firefighter's eyes. When the goggles are no longer needed, they may be repositioned on the crown of the helmet.

Although goggles provide many safety features, it may often be desired to remove the goggles from the helmet completely. However, prior goggle mounting systems do not provide for easy removal or reattachment of the goggles to the helmet. Under the prior art, when the goggles are to be removed from the helmet, the receiving rings must first be unscrewed from the helmet. This can be inconvenient, since the operation takes time to complete, requires the use of tools (which may not always be immediately available), and requires a firefighter to remove the helmet before the goggles can be removed. Accordingly, there exists the need for a firefighter goggles retention system which can retain the goggles in a position for easy access, allows the goggles to be adjusted to fit over the firefighter's eyes, and is removable to allow the goggles to be easily uncoupled from the helmet.

SUMMARY OF THE INVENTION

The present invention is a goggle retention system that retains the goggles in a convenient position, allows the goggles to fit over the user's eyes, and is relatively easily removable to allow the goggles to be separated from the helmet. In particular, the retention system of the present invention allows for the goggles to be uncoupled by simple hand manipulation.

The goggle retention system of the present invention provides for a plurality of clips which receive and retain the strap of the user's goggles. Each clip has a base mounted to a helmet, and a removable eyelet shaped to receive and retain the goggles. Each base has an oblong slot extending therethrough and is shaped to receive and retain an associated eyelet. Each base further includes a pair of transverse locking notches and a helical camming surface extending between the slot and the notches. Each eyelet includes a generally circular ring to retain the goggle strap, and a pair of spaced, parallel legs extending from the ring. Each eyelet further includes a pair of opposed, spaced feet at the ends of the legs. The feet are shaped to pass through the slot when the feet are oriented lengthwise of the slot. An eyelet is attached to an associated base by passing the feet of the eyelet through the slot of the base and rotating the eyelet so that the narrowing width of the slot urges the legs closer together causing the legs to exert a reactive force against the inside walls of the slot, thereby securing the eyelet to the base, and securing the strap in the eyelet. The system of the present invention allows the goggles to be easily attached or released by simple hand manipulation.

Accordingly, it is an object of the present invention to provide a relatively simple and inexpensive system; a goggle mounting system for releasably attaching a pair of goggles to a helmet; a goggle mounting system which allows the goggles to be attached or released by simple hand manipulation; and a goggle mounting system which is rugged and durable.

Other objects and advantages of the present invention will be apparent from the following description, the accompanying drawings and the appended claims.

DETAILED DESCRIPTION

Figure 1:
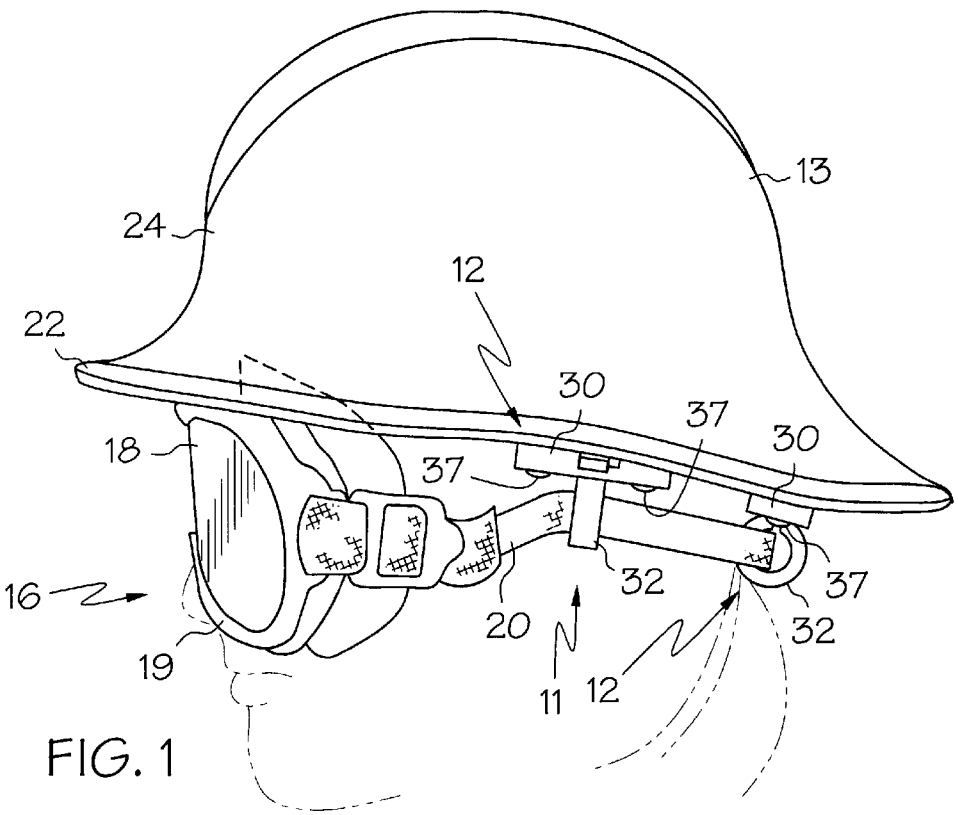
FIG. 1 is a side elevational view of a preferred embodiment of the goggle mounting system of the present invention shown mounted on an associated helmet, along with goggles and a strap.
Figure 2:
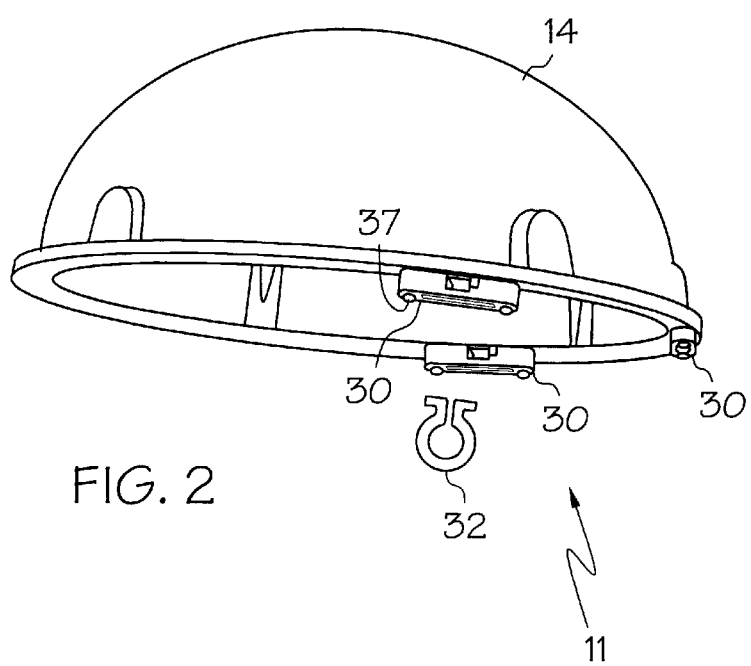
FIG. 2 is a perspective partially exploded view of the goggle retention system of FIG. 1, shown mounted on a helmet liner.

As shown in FIGS. 1 and 2, a preferred embodiment of the goggle retention system of the present invention 11 comprises a plurality of clips, each generally designated 12. Each clip 12 is mounted on the lower open end of a firefighter helmet 13. The firefighter helmet 13 further comprises a firefighter helmet liner 14 which fits inside the helmet. In a preferred embodiment of the present invention, each clip 12 is mounted on the open end of the liner 14. The clips 12 retain a pair of goggles, generally designated 16. The goggles 16 comprise a lens 18, a frame 19, and a strap 20 attached to the frame. The strap 20 is preferably made of an elastic material and is retained by the clips 12 mounted about the lower perimeter of the helmet 13.

In this manner, when the goggles are placed over the firefighter's eyes, as shown in FIG. 1, the strap 20 is retained in clips 12. When the firefighter desires to remove the goggles 16 from his face and temporarily place them out of use, the firefighter may pull the goggles around the brim 22 of the helmet 13, and rest the goggles on the crown 24 of the helmet. In this manner, the goggles 16 are placed out of the firefighter's field of vision, but are retained in a convenient location should the firefighter later wish to use the goggles.

Figure 3:
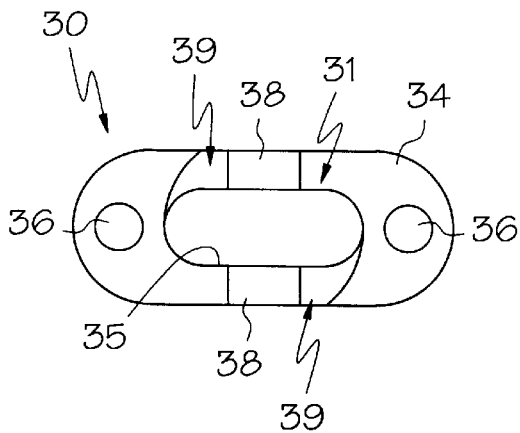
FIG. 3 is a top plan view of a base component of a clip for use with the goggle retention system of FIG. 1.
Figure 4:
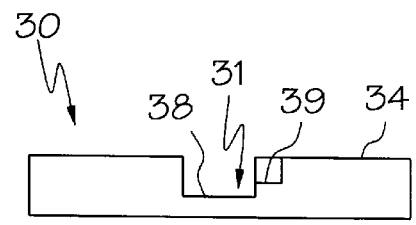
FIG. 4 is a side elevational view of the base component of FIG. 3.

As shown in FIGS. 3 and 4, each clip 12 comprises a base 30 and an eyelet 32. Each base 30 includes an oblong slot 31, extending through the base, and a top face 34. Each slot 31 is defined by an inside wall 35. Each base 30 further includes a pair of holes 36 for receiving mounting screws 37 (see FIGS. 1 and 2). Alternatively, the base 30 may be attached to the helmet 13 or liner 14 by bolts, rivets, or other attachment means.

The base 30 also includes a pair of opposed, rectangular locking notches 38, located on the longitudinal edges of the base 30, and a pair of camming surfaces 39 located adjacent to each locking notch 38 which have a helical contour relative to an axis passing through the center of the slot 31, and extend from the top face 34 to the locking notches 38.

The slot wall 35 has rounded corners to facilitate the rotation of the eyelet 32. The base 30 of the present invention is substantially oval in plan view.

Figure 5:
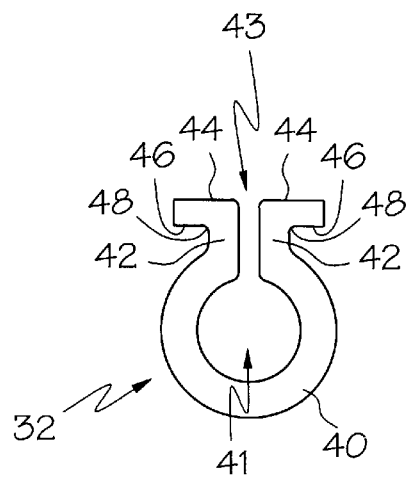
Fig. 5 is a side elevational view of an eyelet component of a clip for use with the goggle retention system of FIG. 1.
Figure 6:
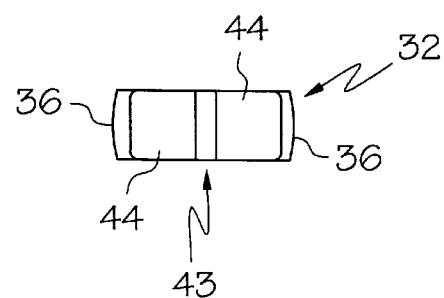
FIG. 6 is a top plan view of the eyelet component of FIG. 5.

As best shown in FIGS. 5–6, each eyelet 32 comprises a generally circular, open ring portion 40 having a central hole 41 and terminating in a pair of spaced, parallel legs 42 extending outwardly from ring 40. The legs 42 extend in a generally radial direction relative to the ring 40. The legs 42 are spaced apart from each other to form a gap 43. Strap 20 is passed through the gap 43 so that it rests in ring 40. In a preferred embodiment, the eyelet 32 has a central hole 41. A pair of splayed feet 44 extend from the ends of the legs 42 in opposite directions, each having an upper bearing surface 46. The feet 44 are shaped and sized to pass through the slot 31 when longitudinally oriented with the length of the slot 31.

The operation of the goggle mounting system 11 is as follows. The bases 30, which are attached to the helmet 13 or the liner 14, are separated from the eyelets 32. To attach the goggles 16 to the helmet 13, strap 20 is inserted through the gaps 43 of each eyelet 32 into the eyelet hole 41. The eyelets 32 are then secured to their respective bases 30 as described below.

Figure 7:
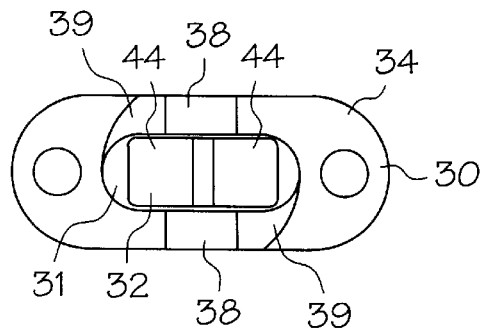
FIG. 7 is a top plan view of a clip for use with the goggle retention system of FIG. 1, shown in an unlocked position.
Figure 8:
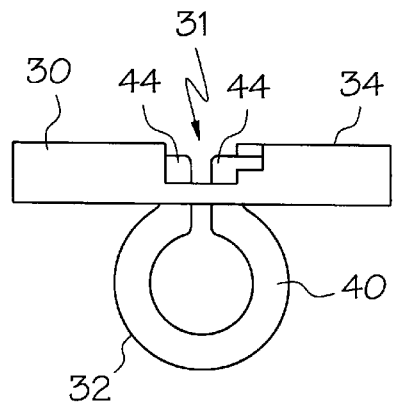
FIG. 8 is a side elevational view of the clip of FIG. 7.
Figure 9:
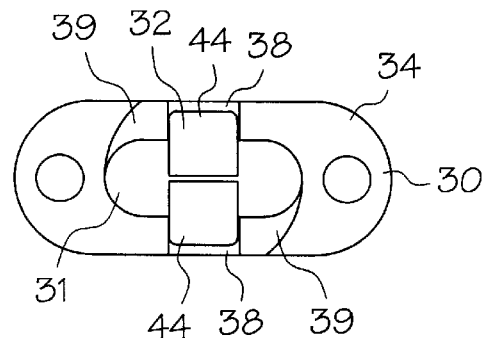
FIG. 9 is a top plan view of a clip for use with the goggle retention system of FIG. 1, shown in a locked position.
Figure 10:
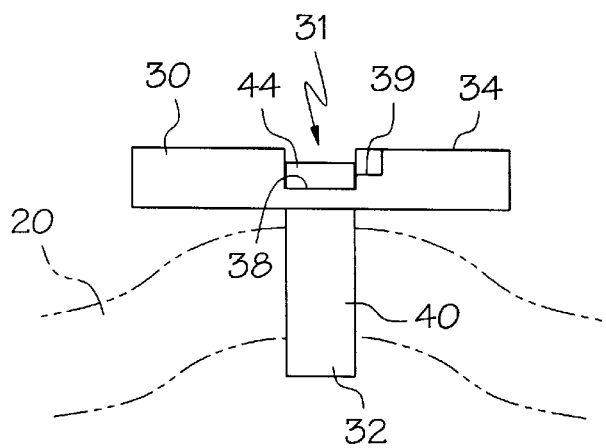
FIG. 10 is a side elevational view of the clip of FIG. 9.

FIGS. 7–10 best illustrate the attachment of a representative eyelet 32 to its base 30. To attach the eyelet 32, the feet 44 of the eyelet 32 are longitudinally oriented within slot 31. FIGS. 7–8 illustrate the eyelet 32 and the base 30 in such a position. In order to lock the eyelet 32 into position, the eyelet is then twisted approximately 90° clockwise. As the eyelet 32 is twisted, such that the upper surfaces 46 bears against the helical camming surfaces 39, which draws the eyelet 32 into the base 30 and the feet into the locking notches 38, as shown in FIG. 9. When the eyelet 32 is twisted so that the legs 42 are transverse to the slot 31, the engagement of the outer surfaces 48 (see FIG. 5) of the legs against the wall 35 causes gap 43 to narrow. The resiliency of the eyelet 32 causes the legs 42 to exert a force against the inside walls 35 of the slot 31, which secures the eyelet within the base 30.

To detach the eyelet 32 from the base 30, the eyelet 32 is pushed in and twisted approximately 90° in a counter-clockwise direction such that the feet 44 are oriented lengthwise in the slot 31. The eyelet 32 is then extracted from the base 30. The twisting of the eyelet may be accomplished through simple hand manipulation, and therefore no tools are required. Similarly, the helmet does not need to be removed from the firefighter's head in order to attach or detach the eyelet 32 to the base 30 since the firefighter may simply reach up to each eyelet 32 and twist to unlock it.

In a preferred embodiment of the invention, spiral notches 39 are utilized to guide the feet 40 during their rotation. When the eyelet is in the locked position, the feet 40 further preferably rest within the rectangular notches 38. The notches 38 allow the feet 40 to be recessed from the top face 34 of the base so that the feet 40 do not abut against the helmet 12 or the liner 14. Each clip 12 of the present invention is preferably fabricated of a strong yet durable plastic such as nylon.

In an alternate embodiment of the invention (not shown), the legs and feet may be integrally formed with the strap and directly extend out of strap. No ring or corresponding element is utilized in this alternate embodiment.

While the present invention is described herein for use with a firefighter helmet, it is to be understood that the method and goggle mounting system of the present invention may be used in conjunction with any helmet, hat, or head covering wherein goggles or other face protection having a strap is used. For example, hard hats, motorcycle helmets, racing helmets, or military headgear may all be used with the goggle retention system of the present invention.

While the form of apparatus herein described constitutes a preferred embodiment of the invention, it is to be understood that the present invention is not limited to this precise form and that changes may be made therein without departing from the scope of the invention.

What is claimed is:

1. A goggle mounting system for retaining a pair of goggles to a helmet, said goggles having an eyepiece and a strap, the mounting system comprising:

a plurality of clips, each clip including:
 a base shaped to be mounted to said helmet, said base including a slot extending therein; and
 an eyelet shaped to receive and retain said strap and including a pair of legs extending therefrom and adapted to be received into said slot in said base, each of said legs having a projection extending therefrom adapted to engage a retaining surface of said base upon rotation of said lees in said slot.

2. A system for retaining a pair of goggles to a helmet, said goggles having an eyepiece and a strap, the retaining system comprising:

a plurality of clips, each of said clips being made of a flexible, plastic material, said clips including:
a base shaped to be mounted to said helmet and having an oblong slot therethrough defined by a side wall, a pair of locking notches formed in a top surface of said base and oriented transversely to said slot, and helical camming surfaces extending between said side wall at said top surface and said locking notches; and
an eyelet having a generally circular ring portion sized to retain said strap therein, a pair of spaced, substantially parallel legs extending from said ring and forming a gap communicating with an interior of said ring such that a strap can be inserted through said gap and into said ring interior, said legs each terminating in a foot extending perpendicular to said leg, said feet extending in directions substantially opposite to each other and including upper bearing surfaces;
whereby said eyelet is releasably attachable to said base by aligning said feet lengthwise of said slot and inserting said feet into said slot and rotating said eyelet such that said feet are oriented substantially transversely of said oblong slot, wherein said upper bearing surfaces of said feet bear against said camming surface, said camming surface guiding said feet into said locking notches, and wherein said legs bear against said side wall to retain said eyelet in said base.

3. The system of claim 2 wherein each of said notches is shaped to allow for the rotation of said feet within said notch portion at least approximately 90 degrees.

4. The system of claim 3 wherein each of said slots has rounded corners to facilitate said rotation of said eyelet.

5. The system of claim 4 wherein each of said bases has at least two holes extending therethrough for receiving attaching means for mounting said base to said helmet.

6. The system of claim 5 wherein each of said bases is substantially oval in plan view.

7. The system of claim 6 wherein each of said clips is fabricated of a flexible plastic material.

8. The system of claim 7 wherein said plastic material is nylon.

9. The system of claim 8 wherein each ring includes a hole extending therethrough to receive said strap.

10. A method for retaining a pair of goggles to the lower edge of a helmet, said goggles having an eyepiece and a strap, the method comprising the steps of: selecting at least two clips, each clip having a base shaped to be mounted to said helmet and to receive an eyelet, said base having an oblong slot therethrough, said slot having an inside wall, said clip further including an eyelet having a generally circular ring to retain said strap, a pair of spaced, parallel legs extending from said ring, and a pair of opposed, spaced feet, said feet being shaped to pass through said slot when said feet are oriented lengthwise with said slot;

securing each of said bases to said helmet; passing said feet of each eyelet through an associated one of said slots;

and rotating each of said eyelets, wherein said legs engage said inside wall and are urged together, causing said legs to exert a force on said inside wall of said slot thereby securing each eyelet in an associated base, and securing said strap in said eyelet.

11. The method of claim 10 wherein each base includes a top face having a notch to allow said feet to seat flush with or below said top face upon rotation of said eyelet.

12. The method of claim 11 wherein each notch is shaped to allow for the rotation of said feet within said notch portion at least approximately 90 degrees.

13. The method of claim 12 wherein each slot has rounded corners to facilitate said rotation of said eyelet.

14. The method of claim 13 wherein each base has at least two holes extending therethrough for receiving attaching means for mounting said base to said helmet.

15. The method of claim 14 wherein said step of fixedly securing each base comprises passing attaching means through said and into said helmet.

16. The method of claim 15 wherein each base is substantially oval in plan view.

17. The method of claim 16 wherein each clip is fabricated of hardened plastic.

18. The method of claim 17 wherein said firefighter helmet has a helmet liner, each base being mounted to said helmet liner.

19. The method of claim 18 wherein each ring has a hole extending therethrough to receive said strap.

20. A goggle mounting system for retaining a pair of goggles to a helmet, said goggles having an eyepiece and a strap, the mounting system comprising:

a plurality of clips, each clip including:

a base shaped to be mounted to said helmet; and an eyelet shaped to receive and retain said strap and to be received by said base, said eyelet being attachable to and removable from said base;

wherein each base includes an oblong slot extending therethrough; and wherein each eyelet includes a generally circular ring sized to retain said strap therein, a pair of spaced, parallel legs extending from said ring, and a pair of opposed, spaced feet, said feet being shaped to pass through said slot when said feet are oriented lengthwise with said slot such that said eyelet is placed in a locking position relative to said base by passing said feet through said slot and rotating said eyelet to orient said feet to extend transversely of said oblong slot.

21. The goggle mounting system of claim 20 wherein each base includes a top face having a notch shaped to receive said feet to seat flush with or below said top face upon rotation of said eyelet to said locking position.

22. The goggle mounting system of claim 21 wherein each notch is shaped to allow rotation of said feet within said notch portion at least approximately 90 degrees.

23. The goggle mounting system of claims 22 wherein each slot has rounded corners to facilitate said rotation of said eyelet.

24. A goggle mounting system for retaining a pair of goggles to a helmet, said goggles having an eyepiece and a strap, the mounting system comprising:

a plurality of clips, each clip including, a female clip component adapted to be mounted to said helmet, said female clip component including a slot extending therein; and a male clip component including a pair of legs and a means for retaining said pair of legs to said goggle strap, said legs being adapted to be received into said slot in said female clip component and each of said legs having a projection extending therefrom adapted to engage a retaining surface of said female clip component upon rotation of said legs in said slot.

25. A method for retaining a pair of goggles to a helmet, said goggles having an eyepiece and a strap, the method comprising the steps of:

providing a plurality of eyelet rings, each eyelet ring having an eyelet hole and a gap providing radial access to the eyelet hole;

passing the goggle strap through each of the gaps such that the goggle strap is received within each eyelet hole of each eyelet ring; and removably clipping each eyelet ring to an underside of the helmet, substantially about a ear circumference of the helmet.

26. The method of claim 25, further comprising the step of attaching a plurality of female clip components to the underside of the helmet, substantially about a rear circumference of the helmet, wherein each clip component includes a slot extending therein, wherein said step of removably clipping each eyelet ring to an underside of the helmet includes the step of inserting a male clip component extending from each of the eyelet rings into a respective one of the slots of the female clip components.

27. The method of claim 26, wherein:

each male clip component includes a pair of legs extending radially from a respective eyelet ring, the pair of legs being positioned on opposite sides of the gap;

each of the legs include a projection extending outwardly therefrom; and the step of removably clipping each eyelet ring to an underside of the helmet further includes the step of rotating the male clip component, inserted into a respective slot of a female component, so that the projections extending outwardly from each of the legs engage a retainer surface of the female clip component.

* * * * *